(12) United States Patent
Fitzgerald et al.

(10) Patent No.: US 9,222,949 B2
(45) Date of Patent: Dec. 29, 2015

(54) SALVINORIN IMMUNOASSAY

(75) Inventors: Stephen P. Fitzgerald, Crumlin (GB);
Robert I. McConnell, Crumlin (GB);
Philip A. Lowry, Crumlin (GB);
Elouard Benchikh, Crumlin (GB)

(73) Assignee: RANDOX LABORATORIES, LTD., Crumlin (GB)

( * ) Notice: Subject to any disclaimer, the term of this patent is extended or adjusted under 35 U.S.C. 154(b) by 249 days.

(21) Appl. No.: 12/662,651

(22) Filed: Apr. 27, 2010

(65) Prior Publication Data
US 2010/0291600 A1 Nov. 18, 2010

(30) Foreign Application Priority Data
Apr. 29, 2009 (EP) .................................... 09159094

(51) Int. Cl.
G01N 33/53 (2006.01)
C07K 16/16 (2006.01)
G01N 33/94 (2006.01)

(52) U.S. Cl.
CPC ................ *G01N 33/94* (2013.01); *C07K 16/16* (2013.01); *G01N 33/946* (2013.01)

(58) Field of Classification Search
None
See application file for complete search history.

(56) References Cited

U.S. PATENT DOCUMENTS

| 6,991,911 B2 * | 1/2006 | Zheng et al. ................... 435/7.9 |
| 2006/0058264 A1 | 3/2006 | Prisinzano |
| 2006/0083679 A1 | 4/2006 | Zjawiony et al. |
| 2007/0059272 A1 * | 3/2007 | Alverdy ........................ 424/78.3 |

FOREIGN PATENT DOCUMENTS

WO WO 2005/089745 A1 9/2005

OTHER PUBLICATIONS

Abbiotec Salvinorin Antibody Product Information, 2008, pp. 1-2.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Valdés et al., "Ethnopharmacology of Ska María Pastora (*Salvia divinorum*, Epling and Játiva-M.)," *J. Ethnopharmacology*, vol. 7, 1983, pp. 287-312.
Roth et al., "Salvinorin A: A potent naturally occurring non-nitrogenous κ opioid selective agonist," *PNAS*, vol. 99, No. 18, Sep. 3, 2002, pp. 11934-11939.
Vortherms et al., "Salvinorin A: From Natural Product to Human Therapeutics," *Molecular Interventions*, vol. 6, Issue 5, Oct. 2006, pp. 259-267.
Hooker et al., "Pharmacokinetics of the potent hallucinogen, salvinorin A in primates parallels the rapid onset and short duration of effects in humans," *NeuroImage*, vol. 41, 2008, pp. 1044-1050, Elsevier Inc.
Yan et al., "Salvinorin A: A novel and highly selective κ-opioid receptor agonist," *Life Sciences*, vol. 75, 2004, pp. 2615-2619, Elsevier, Inc.
Schmidt et al., "Determination of Salvinorin A in body fluids by high performance liquid chromatography-atmospheric pressure chemical ionization," *Journal of Chromatography B*, vol. 818, 2005, pp. 221-225, Elsevier B.V.
Schmidt et al., "Pharmacokinetics of the Plant-Derived κ-Opioid Hallucinogen Salvinorin A in Nonhuman Primates," *Synapse*, vol. 58, 2005, pp. 208-210, Wiley-Liss, Inc.
Pichini et al., "Quantification of the plant-derived hallucinogen Salvinorin A in conventional and non-conventional biological fluids by gas chromatography/mass spectrometry after *Salvia divinorum* smoking," *Rapid Communications in Mass Spectrometry*, vol. 19, 2005, pp. 1649-1656, John Wiley & Sons, Ltd.

(Continued)

*Primary Examiner* — Galina Yakovleva

(74) *Attorney, Agent, or Firm* — Oliff PLC

(57) ABSTRACT

The present invention provides an immunoassay method for detecting or determining the amount of salvinorin A, salvinorin B and/or analogues thereof in an in vitro sample, an antibody for salvinorin A, salvinorin B and/or analogues thereof and a kit for detecting the presence of or determining the amount of salvinorin A, salvinorin B and its analogues thereof in a sample.

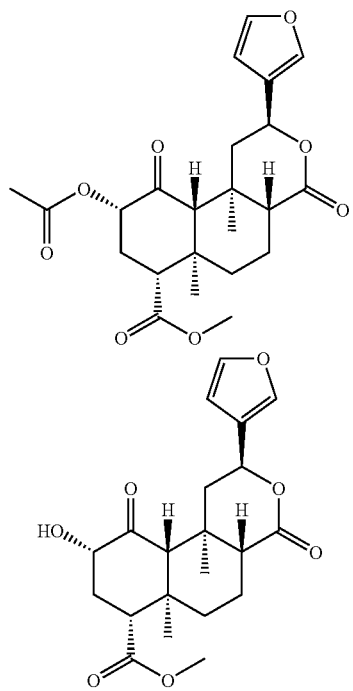

4 Claims, 2 Drawing Sheets

(56) References Cited

OTHER PUBLICATIONS

Tsujikawa et al., "In vitro stability and metabolism of salvinorin A in rat plasma," *Xenobiotica*, vol. 39, No. 5, 2009, pp. 391-398, Informa UK Ltd.

Imai et al., "Substrate Specificity of Carboxylesterase Isozymes and Their Contribution to Hydrolase Activity in Human Liver and Small Intestine," *Drug Metabolism and Disposition*, vol. 34, No. 10, 2006, pp. 1734-1741, The American Society for Pharmacology and Experimental Therapeutics.

Grundmann et al., "*Salvia divinorum* and Salvinorin A: An Update on Pharmacology and Analytical Methodology," *Planta Med*, vol. 73, 2007, pp. 1039-1046, Georg Thieme Verlag KG Stuttgart, New York.

McDonough et al., "The Detection and Quantitative Analysis of the Psychoactive Component of *Salvia divinorum*, Salvinorin A, in Human Biological Fluids Using Liquid Chromatography-Mass Spectrometry," *Journal of Analytical Toxicology*, vol. 32, Jul./Aug. 2008, pp. 417-421.

* cited by examiner

Synthesis of Salvinorin A-7-hemisuccinate (Hapten A)

Figure 1

Immunogen Ia (left) a Hapten B (right)

SALVINORIN IMMUNOASSAY

FIELD OF THE INVENTION

The present invention relates to the field of drug analysis and determination. Specifically, the present invention relates to an immunoassay for the detection and determination of salvinorin A, salvinorin B and/or analogues thereof and an antibody and kit for use in such methods.

BACKGROUND TO THE INVENTION

The diterpenoid, salvinorin A is a potent psychoactive component of the indigenous Mexican plant *Salvia divinorum* used medicinally by the Mazatec Indians for treating headaches, arthritis and anaemia (Valdes et al. 1983). The CNS activity of this normitrogenous molecule is attributed to its strong affinity for the kappa-opiod receptor (KOR) (Roth et al 2002). Its use as a recreational drug is increasing due to its ready availability and potent activity. Ingestion of *S. divinorum* or salvinorin A (from here-on, reference to salvinorin A use or ingestion implicitly includes *S. divinorum*) is usually by way of leaf chewing, intake of a liquid extract of the leaves or smoke inhalation. Its CNS effects and hallucinogenic properties have been compared to LSD, leading to its illegal status in many countries. The KOR has been implicated in nociception and a number of disease processes, and there is great interest in the active ingredient of *S. divinorzam*, salvinorin A (and its analogues) as a potential treatment for various conditions including diarrhoea, mood disorders, and in the regulation of pain (Vortherms and Roth, 2006). The use of salvinorin A and analogues as a potential treatment for mania is described in WO 2005/089745; US 2006/0058264 describes salvinorin A and analogues as useful compounds for pharmacological research purposes and for disease treatment; US 2006/0083679 proposes the use of salvinorin A and analogues as medicines or as chemical probes in diagnostic procedures such as PET, SPECT and NMR spectroscopy. This interest has resulted in the synthesis and pharmacological study of various salvinorin analogues. More recently, C-9 ether derivatives of salvinorin A have been shown to be more active and have a greater half-life than salvinorin A. This development has generated interest in the scientific research community regarding potential new therapeutic drugs, although the broader societal consequences of the abuse of such potent CNS-active molecules are unknown.

The short action of duration of salvinorin A (approximately 10-15 minutes) suggests rapid metabolism to an inactive form. Phamacokinetic studies by Hooker et al (2008) using PET supported the rapid uptake and short duration of action of salvinorin A. The C-9 hydroxylated analogue, salvinorin B, is speculated to be the main metabolite formed by esterase-mediated hydrolysis (Yan and Roth 2004; Schmidt et al 2005a). Studies by Schmidt et al (2005a, 2005b) on monkey plasma were inconclusive as the ex vivo study identified salvinorin B as a metabolite, while the in vivo study did not detect salvinorin B. Pichini et al (2005) were unable to detect salvinorin A in the saliva, sweat or urine of patients 1.5 hours after they had smoked the drug, suggesting either rapid elimination or extensive metabolism. Tsujikawa et al (2009), in an in vitro metabolic study using rat plasma, identified salvinorin B and 1,4a-dimethyl-l-[2-(3-furanyl)-2-hydroxyethyl]-7-hydroxy-5-methoxycarbonyl-8-oxodecahydronapthalene-2-carboxylic acid as the main metabolites. Thus, although there is mounting evidence that salvinorin B is the main metabolite of salvinorin A, besides the metabolites proposed by Tsujikawa, there are likely to be as yet unidentified metabolites. A comparative analysis of the metabolic pathway of other psychoactive drugs with similar molecular structures, methods of ingestion and pharmacological properties enables predictions of other possible salvinorin A metabolites. Drug metabolism usually involves the formation of more polar substances to facilitate excretion. This occurs through first-phase (blood-based) oxidation mediated by cytochrome P450 enzymes and second-phase (liver-based) glucuronidation. The structural and pharmacological similarities of salvinorin A and $\Delta^9$-THC, as well as their similar methods of ingestion, suggests metabolic data derived from $\Delta^9$-THC research might be a useful indicator of the likely metabolic products of salvinorin A. One metabolite of $\Delta^9$-THC is the primary alcohol 11-hydroxy-$\Delta^9$-THC, formed through oxidation of the methyl group attached to the alkene group of the heterocyclic system. The primary alcohol is further oxidised to the main metabolite of $\Delta^9$-THC, 11-nor-$\Delta^9$-THC-9-carboxylic acid which also undergoes glucuronidation. Cocaine and heroin, potent CNS-acting drugs, like salvinorin A, each possess two ester functionalities and the metabolic pathways of the three drugs might be expected to show similarities. Cocaine and heroine are metabolized by human carboaylesterases (hCEs), enzymes expressed in various organs including the liver, intestines and lungs (Imai et al 2006}. Based on comparative scientific evidence and pharmacological properties of salvinorin A and its analogues, salvinorin A-7-carboxylic acid and salvinorin B-7-carboxylic acid are potential metabolites of salvinorin A.

Several analytical methods have been devised to detect and quantify salvinorin A and its analogues in *S. divinorum* (Grundmann et al 2007). Besides the rat plasma study of Tsujikawa, detection in animal fluids has been limited to the detection of salvinorin A and salvinorin B. Schmidt et al (2005a) used HPLC-MS to detect salvinorin A and salvinorin B in monkey plasma samples ex vivo. They reported that salvinorin B could not be clearly detected in in vivo samples. Pichini et al (2005) used GC-MS to analyse the urine, saliva and sweat of two individuals who had smoked *S. divinorum* leaves. As previously described, salvinorin A was detected in urine within the first 1.5 hours (limit of detection was 5 ng/ml). After 1.5 hours the technique did not detect salvinorin A in either urine or saliva, probably limited by the sensitivity of the assay. McDonough et al (2008) developed a HPLC-MS to detect and quantitate salvinorin A in human biological fluids stating previously described methods as irreproducible. The method had a limit of detection of 2.5 ng/ml and a limit of quantitation of 5.0 ng/ml. They also suggested that due to rapid disappearance of salvinorin A, identification of a metabolite of the primary active substance is desirable.

To enable a robust detection method which identifies the use of salvinorin A, provision must be made to detect not only recognised markers such as the parent salvinorin A and C-9 metabolite salvinorin B, but also, as yet unidentified metabolites. In addition this method must be highly sensitive to salvinorin A, the one unequivocal marker of salvinorin A use. A highly sensitive and relatively simple method for detecting the ingestion of salvinorin A by the in vitro analysis of human biological samples has so far not been developed. Furthermore, therapeutic research has already identified, and will continue to identify, highly active analogues of salvinorin A which the recreational drug taker will exploit.

It is evident that existing assay formats for the detection of salvinorin A are inadequate, and do not enable such robust detection. Know detection methods use expensive equipment which have low sensitivity for salvinorin A and hence a limited window of detection following salvinorin A ingestion. Furthermore, these assays do not address detection of new and future synthetic analogues of greater stability and activity than salvinorin A. Thus methods are also required to detect the next generation of salvinorin A based drugs.

SUMMARY OF THE INVENTION

The invention provides a solution to the problems posed by the prior art relating to the analytical detection and determination of salvinorin A, salvinorin B, their analogues and/or metabolites. The invention has particular application in the area of therapeutic drug development and illicit drug use.

"Detection" means the qualitative analysis of the presence or absence of salvinorin A, salvinorin B, their analogues and/or metabolites.

"Determination" means quantitative analysis of the amount of salvinorin, salvinorin B, their analogues and/or metabolites. The present invention provides highly sensitive and generic antibodies raised from novel immunogens enable methods and antibody-based analytical kits which,
- are more than 100-fold more sensitive towards salvinorin A than existing analytical methods;
- enable the detection and determination of active analogues of salvinorin A such as 9-methoxymethyl-salvinorin B; and
- enable the detection and determination of salvinorin A metabolites such as salvinorin B.

Thus, in a first aspect, the present invention provides a method for detecting or determining the amount of salvinorin A, salvinorin B and/or a C-9 analogue of salvinorin A and/or salvinorin B in an in vitro sample, the method comprising contacting the sample with an antibody, detecting antibody bound to salvinorin A, salvinorin B and/or a C-9 analogue of salvinorin A and/or salvinorin B, and deducing from a calibration curve the presence or the amount of salvinorin A, salvinorin B and/or a C-9 analogue of salvinorin A and/or salvinorin B, wherein the antibody is raised from an immunogen of the following structure:

Immunogen I wherein accm is an antigenicity-conferring carrier material and the crosslinker joins the O-atom at C-9 of the tricyclic fused ring to the accm.

In a second aspect the present invention provides a method for detecting or determining the amount of salvinorin A, salvinorin B and/or a C-7 analogue of salvinorin A and/or salvinorin B in an in vitro sample, the method comprising contacting the sample with an antibody, detecting antibody bound to salvinorin A, salvinorin B and/or a C-7 analogue of salvinorin A and/or salvinorin B, and deducing from a calibration curve the presence or the amount of salvinorin A, salvinorin B and/or a C-7 analogue of salvinorin A and/or salvinorin B, wherein the antibody is raised from an immunogen of the following structure Immunogen II wherein R=H or acetyl, accm is an antigenicity-conferring carrier material and the crosslinker joins the carbonyl group at C-7 of the tricyclic fused ring to the accm.

In a third aspect the present invention provides a method for detecting the presence of or determining the amount of one or more molecules selected from the group consisting of 2-{(1R,2R,4aR,5R,7S,8aR)-1,4a-dimethyl-1-[(S)-2-(3-furanyl)-2-hydroxyethyl]-7-hydroxy-5-methoxycarbonyl-8oxo-decahydronapth-2-yl}ethanoic acid, 2-{(1R,2R,4aR,5R,7S,8aR)-1,4a-dimethyl-1-[(S)-2-(3-furanyl)-2-hydroxyethyl]-5-carboxy-7-hydroxy-8-oxodecahydronapth-2-yl}ethanoic acid, 2-{(1R,2R,4aR,5R,7S,8aR)-1,4a-dimethyl-1-[(S)-2-(3-furanyl)-2-hydroxyethyl]-7-acetoxy-5-carboxy-8-oxo-decahydronapth-2-yl}ethanoic acid or 2-{(1R,2R,4aR,5R,7S,8aR)-1,4a-dimethyl-1-[(S)-2-(3-furanyl)-2-hydroxyethyl]-7-acetoxy-5-methoxycarbonyl-8-oxodecahydronapth-2-yl}ethanoic acid in an in vitro sample, the method comprising contacting the sample with an antibody, detecting antibody bound to the one or more molecules, and deducing from a calibration curve the presence or the amount of the one or more molecules wherein the antibody is raised from an immunogen of the following structure Immunogen III wherein R=H or
acetyl and $R_1$=OH or CH3-O—, accm is an antigenicity-conferring carrier material and the crosslinker joins the carbonyl group at C-2 of the bicyclic fused ring to the accm.

In a fourth aspect the present invention provides an antibody raised against an immunogen as described in the first aspect of the present invention, wherein the antibody is capable of binding with at least one structural epitope of salvinorin A, salvinorin B and/or C-9 analogues of salvinorin A and/or salvinorin B. Preferably the C-9 analogues is selected from 9-methoxymethylethersalvinorin B and/or 9-ethoxymethylethersalvinorin B.

In a fifth aspect, the present invention provides an antibody against an immunogen described in the second aspect of the present invention, the antibody being capable of binding with at least one structural epitope of salvinorin A, salvinorin B, and/or a C-7 analogue of salvinorin A and/or B.

In a sixth aspect the present invention provides an antibody raised against an immunogen described in the third aspect of the present invention, wherein the antibody is capable of binding with at least one structural epitope of 2-{(1R,2R,4aR,5R,7S,8aR)-1,4a-dimethyl-1-[(S)2-(3-furanyl}2-hydroxyethyl]-7-hydroxy-5-methoxycarbonyl-8-oxodecahydronapth-2-yl}ethanoic acid, 2-{(1R,2R,4aR,5R,7S,8aR)-1,4a-dimethyl-1-[(S)-2-(3-furanyl)-2-hydroxyethyl]-5-carboxy-7-hydroxy-8-oxodecahydronapth-2-yl}ethanoic acid, 2-{(1R,2R,4aR,5R,7S,8aR)-1,4a-dimethyl-1-[(S)-2-(3-furanyl)-2-hydroxyethyl]-7-acetoxy-5-carboxy-8-oxo-decahydronapth-2-yl}ethanoic acid or 2-{(1R,2R,4aR,5R,7S,8aR)-1,4a-dimethyl-1[(S)-2-(3-furanyl)-2-hydroxyethyl)-7-acetoxy-5-methoxycarbonyl-8-oxodecahydronapth-2-yl}ethanoic acid.

In a seventh aspect, the present invention provides a kit for detecting the presence of or determining the amount of salvinorin A, salvinorin B and/or C-9 analogues of salvinorin A and/or salvinorin B, the kit including at least one antibody of the fourth aspect of the present invention.

In a eighth aspect the present invention provides a kit for detecting the presence of or determining the amount of salvinorin A and/or C-7 analogues of salvinorin A, the kit including at least one antibody of the fifth aspect of the present invention.

In a ninth aspect the present invention provides a kit for detecting the presence of or determining the amount of 2-{(1R,2R,4aR,5R,7S,8aR}-1,4a-dimethyl-1[(S)-2-(3-furanyl)-2-hydroxyethyl]-7-hydroxy-5-methoxycarbonyl-8-oxodecahydronapth-2-yl}ethanoic acid, 2-{(1R,2R,4aR,5R,7S,8aR)-1,4a-dimethyl-1-[(S)-2-(3-furanyl)-2hydroxyethyl]-5-carboxy-7-hydroxy-8-oxodecahydronapth-2-yl}ethanoic acid, 2-{(1R,2R,4aR,5R,7S,8aR)-1,4a-dimethyl-1-[(S)-2-(3-furanyl)-2-hydroxyethyl)-7-acetoxy-5-carboxy-8-oxodecahydronapth-2-yl}ethanoic acid or 2-{(1R,2R,4aR,5R,7S,8aR)-1,4a-dimethyl-1-[(S)-2-(3-furanyl}2-hydroxyethyl)-7-acetoxy-5-methoxycarbonyl-8-oxodecahydronapth-2-yl}ethanoic acid, the kit including at least one antibody of the sixth aspect of the present invention.

BRIEF DESCRIPTION OF THE DRAWINGS

The invention will now be described by way of examples with reference to the following figures in which:
FIG. 1 shows schematically the synthesis of Salvinorin A-7-hemisuccinate (Hapten A)

DETAILED DESCRIPTION OF THE INVENTION

Figure 2:
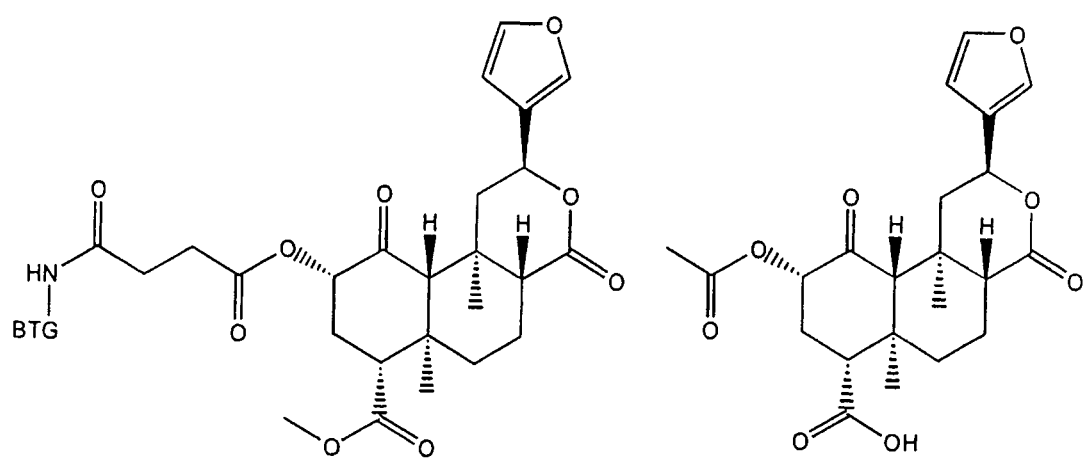
FIG. 2 shows immunogen Ia and Hapten B

The antibody used in the present invention is raised from an immunogen comprising at least one structural epitope of salvinorin A, salvinorin B or analogues thereof. The immunogen comprises a hapten of salvinorin A, salvinorin B or an analogies thereof linked by a crosslinker to an antigenicity-conferring carrier material. The crosslinker is preferably of the structure —$(X)_n$—Y—Z—, where n=0 or 1, and if present, X is selected from the group consisting of carbonyl, thiocarbonyl, oxycarbonyl or oxythiocarbonyl; Y is preferably a $C_1$-$C_{10}$ substituted or unsubstituted straight chain or saturated alkylene moiety, or an arylene moiety; and Z (before conjugation with the antigenicity-conferring carrier material) is preferably a carboxy, a dithiopyridyl, a maleimide, amino, hydroxyl, thiol, thioester or an aldehyde moiety. More preferably, X is a $C_2$-$C_6$ substituted or unsubstituted straight chain or saturated alkylene moiety and Z is a carboxy or amino moiety. In a preferred embodiment, the method involves the use of the immunogen salvinorin B-9S-hemisuccinate-NH-BTG (Immunogen Ia of FIG. 2). Crosslinkers for use in immunogen formation by joining haptens to antigenicity-conferring carrier materials are well known to the person skilled in the art. Such crosslinkers are often made up of a substituted or unsubstituted chain of 2-10 carbon atoms which may or may not incorporate ring systems. By C-9 analogues it is meant molecules of the salvinorin A or salvinorin B structure with modification only at the C-9 position. By C-7 analogues it is meant molecules of the salvinorin A or salvinorin B structure with modification only at the C-7 position. A hapten is defined as a non-immunogenic molecule and for the purpose of this patent includes salvinorin A, salvinorin B and their derivatives with or without the crosslinker.

The crosslinker used in the methods of the invention prior to conjugation is preferably succinic anhydride or tert-butyl aminoethanoate. Preferably, the accm is a protein, a protein fragment, a synthetic polypeptide or a semi-synthetic polypeptide. Illustrative examples of useful carrier materials are bovine serum albumin (BSA), egg ovalbumin, bovine gamma globulin, bovine thyroglobulin (BTG), keyhole limpet haemocyanin (KLH) etc. Alternatively, synthetic poly (amino acids) having a sufficient number of available amino groups, such as lysine, may be employed, as may other synthetic or natural polymeric materials bearing reactive functional groups. In particular, carbohydrates, yeasts or polysaccharides may be conjugated to the hapten to produce an immunogen.

Conjugates which may be used in the method are well known to the person skilled in the art. Preferably the conjugate is a molecule incorporating or attached to a detectable element, the molecule being able to bind with an antibody raised to an immunogen described in the methods of the invention. The conjugate, when incorporating a labelling agent, can be a radioactive substance. The labelling agent of a conjugate, to which the molecule is attached, is preferably an enzyme, more preferably a peroxidase, most preferably horseradish peroxidase (HRP). When relevantly stimulated, the electromagnetic radiation emitted by the labelling agent changes, and this change is detected and optionally measured. For HRP, the change in electromagnetic radiation is the emission of visible light produced by a chemical reaction (chemiluminescence).

Furthermore, the invention describes a kit for detecting or determining salvinorin A and salvinorin B metabolites in which the lactone ring of salvinorin A and salvinorin B has been opened, the kit including at least one antibody raised from Immunogen III being capable of binding with at least one structural epitope of salvinorin A and salvinorin B metabolites in which the lactone ring of salvinorin A and salvinorin B has been opened.

The kit(s) of the invention may optionally include instructions for use for detecting the target analytes in an in vitro sample. Preferably, the sample is a solution, such as a biological fluid. More preferably, the sample is serum, plasma or urine.

Preferably, the conjugate and salvinorin A, its analogues and metabolites compete for antibody binding sites in a competitive ELISA format. The assay for salvinorin A, its analogues and metabolites may be a single analyte assay such as a dipstick or the microtitre-based ELISA format or it may be part of a multi-analyte assay, in which a suitable substrate such as a biochip supports various analyte-specific antibodies, the various analytes detected and measured using a suitable analyzer system such as "EvidenceT'" or "Evidence InvestigatorT'".

In order to generate polyclonal antisera, the immunogen of the present invention is mixed with Freund's Adjuvant and the mixture is injected into a host animal, preferably a vertebrate animal, most preferably a mammalian animal, such as rabbit, sheep, mouse, guinea pig or horse. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding. Preferably, the antibodies are polyclonal. Alternatively, the antibodies are monoclonal.

The invention will now be described by way of general methods and specific examples.

EXAMPLES

Immunogen formation involves conventional conjugation chemistry in which the oxygen of the hydroxyl group of a hapten combines first with DCC and then NHS to form an ester with a powerful leaving group. Nucleophilic attack on the carbonyl of the ester functionality by a free amine group on the protein (BSA or BTG) results in an amide bond and formation of the target immunogens. Formation of the hapten-HRP conjugate follows a similar mechanism using EDC and sulfo-NHS. For the coupling of crosslinkers to haptens and accms, and haptens to labelling agents to form conjugates, the skilled reader is referred to Bioconjugate Techniques G. Hermanson, ed., Academic Prtss, 1996, 785 pp., the contents of which is incorporated in its entirety.

In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS). MALDI-TOF MS was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1mg/ml sample solutions. Aliquots (1 pl) were analysed using a matrix of Sinapinic acid and bovine serum albumin (Fluka) was used as an external calibrant.

Example 1

Extraction of Salvinorin A from *Salvia divinorum*

Dried *Salvia divinorum* leaves (0.5 kg) were ground to a fine powder and treated with acetone (5×1.5 l). The acetone extract was evaporated to dryness under reduced pressure to afford a crude green gum, which was subjected to column chromatography on silica gel using hexane/ethylacetate (90%/10%) as mobile phase to give a mixture of salvinorin A, salvinorin B and other minor products. This green crude product obtained was recrystallized from isopropanol to give Salvinorin A (2.2 g).

M.P: 231-236; $^{13}$C-NMR (125 MHz, DMSO): δ 202.5, 172.1, 171.5, 169.5, 144.4, 140.6, 126, 109.2, 73.3, 71.4, 61.6, 52.1, 52, 49.9, 42.7, 41.8, 37.6, 35.2, 30.7, 20.8, 18.2, 16.3, 15.1; TLC: Rf=0.32 (EtOAc:hexane, 50:50)

Example 2

Preparation of Salvinorin B

To a solution of Salvinorin A (500 mg, 1.15 mM) in methanol (10 ml) was added solid sodium carbonate (490 mg, 4.6 mM) and the mixture stirred at room temperature overnight. Water (20 ml) was added to mixture and the mixture stirred for 30 mins. The solution was filtered and the filter-cake washed with ice-cold water (20 ml) and ice-cold methanol (20 ml) and dried in a dessicator to give Salvinorin B (191 mg, 42%).

MR: 241-248 C; $^{13}$C-NMR (125 MHz, DMSO): δ 209.3, 172.2, 171.4, 144.2, 139.8, 125.7, 108.7, 74.8, 72.3, 64.2, 53.6, 52.3, 51.8, 44, 43, 38.5, 35.8, 35, 18.6, 16.5, 15.7; TLC: Rf=0.21 (EtOAc:hexane, 50:50).

Example 3

Preparation of Salvinorin Hemisuccinate (Hapten A—FIG. 1)

To Salvinorin B (190 mg, 0.487 mmol) and succinic anhydride (112 mg, 2.5 eq) suspended in dichloromethane (5 ml) at 0° C. was added DBU (218 pl, 3 eq) dropwise. The mixture was stirred at 0° C. for 15 mins, washed with 3% citric acid (5 ml), saturated NaHCO$_3$ solution (5 ml) and brine (5 ml). The mixture was dried over sodium sulfate, filtered and evaporated to dryness. The crude residue was purified by column chromatography (silica gel: CH$_2$Cl$_2$ to 5% MeOH in CH$_2$Cl$_2$) to give salvinorin hemisuccinate (130 mg, 54%).

Example 4

Conjugation of Hapten A to BSA

Hapten A was conjugated to bovine serum albumin (BSA) via EDC/NHS according to standard procedures. EDC Hydrochloride (105 mg) was dissolved in water (0.5 ml) and immediately added to a solution of hapten A (73.6 mg, 0.15 mmol) in DMF (1 ml). After mixing, this solution was added to a solution of BSA (200 mg) in water (10 ml). N-hydroxysuccinimide (NHS) (22.5 mg) was immediately added and the reaction mixture was incubated and stirred overnight at room temperature. The mixture was then dialysed against 50 mM phosphate buffer pH 7.2 (3 changes) for 24 hr, and freeze-dried. Maldi results showed a molecular ratio for hapten A:BSA of approximately 17:1.

Example 5

Conjugation of Hapten A to BTG (Immunogen—FIG. 2)

EDC Hydrochloride (95 mg) was dissolved in water (0.5 ml) and immediately added to a solution of hapten A (66.2 mg, 0.14 mmol) in DMF (1 ml). After mixing, this solution was added to a solution of BTG (150 mg) in water (10 ml). N-hydroxysuccinimide (NHS) (25 mg) was immediately added and the reaction mixture was incubated and stirred overnight at room temperature. The mixture was then dialysed against 50 mM phosphate buffer pH 7.2 (3 changes) for 24 hr, and freeze-dried.

Example 6

Synthesis of Hapten B (FIG. 2)

Lithium iodide (1.52 g, 11.4 mmol) was added to a solution of Salvinorin A (1 g, 2.3 mmol) in dry pyridine (20 ml). The reaction mixture was protected from light by aluminium paper and heated at reflux for 36 hr. The mixture was evaporated to dryness under vacuum, and the residue treated with ice-cold water and acidified to pH 4 to 5 using 1M HCL followed by extraction with ethyl acetate (3×100 ml). The combined organic layers were washed with water, dried over anhydrous $Na_2SO_4$, filtered and evaporated to dryness. The crude residue was purified by column chromatography (silica gel: 50% EtOAc in hexane, to 100% EtOAc) to give Hapten B (140 mg) and Hapten C (151 mg). TLC: Hapten B, Rf=0.28 (Ethyl acetate).

Example 7

Conjugation of Hapten B to BSA

EDC Hydrochloride (90 mg) was dissolved in water (0.5 ml) and immediately added to a solution of hapten B (41.3 mg, 0.098 mmol) in DMF (1 ml). After mixing, this solution was added to a solution of BSA (150 mg) in water (10 ml). N-hydroxysuccinimide (NHS) (20 mg) was immediately added and the reaction mixture was incubated and stirred overnight at room temperature. The mixture was then dialysed against 50 mM phosphate buffer pH 7.2 (3 changes) for 24 hr, and freeze-dried. Maldi results showed a molecular ratio for hapten B:BSA of approximately 4.3:1

Example 8

Conjugation of Hapten A to HItP (Conjugate I)

EDC.HCl (1.5 mg) was dissolved in water (0.5 ml) and immediately added to a solution of Hapten A (3 mg) in DMF (0.3 m}). After mixing for 2 h, the solution was added dropwise to a solution of HRP (20 mg) in phosphate-buffered saline (1.8 ml, pH 8). The mixture was incubated in a dark at room temperature overnight. Excess hapten was removed by desalting with PD-10 columns (Pharmacia) in series, pre-equilibrated with PBS (phosphate buffered saline) at pH 7.2. The hapten-HRP conjugate was dialysed overnight against 10 L of PBS (pH 7.2) at 4° C., filtered and stored a –20° C.

Example 9

Development of ELISAs for Salvinorin A and Salvinorin B

Immunogen Ia was administered to adult sheep on a monthly basis to provide target specific polyclonal antisera. IgG was extracted from the antisera via Caprylic acid/ammonium sulphate precipitation of immunoglobulin. Microtitre plates (Thermo Scientific, 95029180) were coated with antibody (125 μl in a coating buffer of 10 mM Tris, pH 8.5) at 37° C. for 2 hours. Antibody was coated at 2.5 μg/ml. The plates were then washed, 50 μl of sample and calibrator (salvinorin A and salvinorin B prepared at Randox Laboratories) was added to the appropriate wells in triplicate, followed by 75 μl of Conjugate I (at ¹⁄₁₂₈ k) and incubated at 25° C. for 1 hour. The plates were then washed and 125 μl of TMB was added to each well and left at room temperature for 20 mins in the dark. The reaction was stopped using 125 μl of 0.2M sulphuric acid. The absorbencies were then read at 450 nm with an ELISA Microplate reader (BIO-TEK Instruments, EL340) and the means calculated. Antibody specificity and sensitivity were then determined.

The present invention is not limited to the embodiments described herein, which may be amended or modified without departing from the scope of the present invention.

Bibliography

Grundmann O. et al. (2007). *Planta Med.*, 73: 1046
Hooker J. M. et al. (2008). *Neuroimage*, 41: 1044-1050
Imai T. et al. (2006). *Drug Metab. Dispos.*, 34: 1734-1741
McDonough P. C. et al. (2008). *J. Anal. Toxicol.*, 32: 417-421
Pichini S et al. (2005). *Rap. Commun. Mass Spectr.*, 19: 1649-1656
Roth B. L. et al. (2002). *Proc. Natl. Acad. Sci.*, 99: 11934-11939
Schmidt M. S. et al. (2005a). *J. Chromatography B*, 818: 221-225
Schmidt M. D. et al. (2005b). *Synapse*, 58: 208-210
Valdes, L. J. et al. (1983). *J. Ethnopharmacol.*, 7: 287-312
Vorfherms T. A. and Roth, B. L. (2006). *Molec. Intervent.*, 6: 257-265
Tsujikawa K. et al. (2009). *XenoUiotica*, 39: 391-398
Yan F. and Roth B. L. (2004). *Life Sci.*, 75: 2615-2619

TABLE 1

Data generated from competitive microtiter plate assay for salvinorin A and salvinorin B employing antisera generated to Immunogen I (hapten A-BTG).
Table 1: Data generated from competitive microtiter plate assay for salvinorin A and salvinorin B employing antisera generated to Immunogen I (hapten A-BTG)

| Calibrator | Conjugate I | | | | Conjugate II | | | |
|---|---|---|---|---|---|---|---|---|
| Concentration | Salvinorin A | | Salvinorin B | | Salvinorin A | | Salvinorin B | |
| (ng/ml) | $A_{450}$ | % $B/B_0$ | $A_{450}$ | % $B/B_0$ | $A_{450}$ | % $B/B_0$ | $A_{450}$ | % $B/B_0$ |
| 0 | 2.032 | 100 | 2.026 | 100 | 2.410 | 100 | 2.347 | 100 |
| 0.16 | 1.255 | 62 | 1.700 | 84 | 1.540 | 64 | 1.993 | 85 |
| 0.31 | 0.970 | 48 | 1.502 | 74 | 1.221 | 51 | 1.837 | 78 |
| 0.63 | 0.724 | 36 | 1.428 | 70 | 0.947 | 39 | 1.675 | 71 |
| 1.25 | 0.520 | 26 | 1.275 | 63 | 0.716 | 30 | 1.433 | 61 |

TABLE 1-continued

Data generated from competitive microtiter plate assay for
salvinorin A and salvinorin B employing antisera generated to
Immunogen I (hapten A-BTG).
Table 1: Data generated from competitive microtiter plate assay
for salvinorin A and salvinorin B employing antisera generated to
Immunogen I (hapten A-BTG)

| Calibrator | Conjugate I | | | | Conjugate II | | | |
|---|---|---|---|---|---|---|---|---|
| | Salvinorin A | | Salvinorin B | | Salvinorin A | | Salvinorin B | |
| Concentration (ng/ml) | $A_{450}$ | % $B/B_0$ | $A_{450}$ | % $B/B_0$ | $A_{450}$ | % $B/B_0$ | $A_{450}$ | % $B/B_0$ |
| 2.50 | 0.373 | 18 | 1.020 | 50 | 0.481 | 20 | 1.189 | 51 |
| 5.00 | 0.272 | 13 | 0.867 | 43 | 0.333 | 14 | 1.005 | 43 |
| 10.00 | 0.180 | 9 | 0.677 | 33 | 0.217 | 9 | 0.779 | 33 |
| $IC_{50}$ | 0.277 ng/ml | | 2.909 | | 0.331 | | 2.758 | |
| % CR | 100 | | 9.52 | | 100 | | 12.00 | |
| AS | 0.013 ng/ml | | | | | | | |
| FS | 0.045 ng/ml | | | | | | | |

$A_{450}$ = absorbance at 450 nm;
B = absorbance at 450 nm at x ng/ml calibrator concentration;
$B_o$ = absorbance at 450 nm at 0 ng/ml calibrator concentration;
$IC_{50}$ = standard concentration which produces 50% $B/B_o$;
% CR = percentage cross-reactivity based on 100% specificity to salvinorin A;
AS = analytical sensitivity (concentration of calibrator at $A_{450}$ of zero standard minus 2 standard deviations, from 20 replicates); and
FS = functional sensitivity (the lowest concentration of calibrator that can be measured with an inter-assay coefficient of variation of <20%, from 20 replicates).

Table 1 shows that the assay recognises both salvinorin A and salvinorin B with a $IC_{50}$ using conjugate I of 0.277 ng/ml and 2.909 ng/ml, respectively. The analytical sensitivity (AS) of the assay for salvinorin A is 0.013 ng/ml, more than 100-fold more sensitive than existing assays.

The invention claimed is:

1. A method for detecting or determining the amount of salvinorin A, salvinorin B, and/or a C-9 analogue of salvinorin A and/or salvinorin B in an in vitro sample, the method comprising:
   contacting the sample with a conjugate and an antibody,
   detecting conjugate bound to salvinorin A, salvinorin B, and/or a C-9 analogue of salvinorin A and/or salvinorin B, and
   deducing from a calibration curve the presence or the amount of salvinorin A, salvinorin B, and/or a C-9 analogue of salvinorin A and/or salvinorin B,
   wherein;
   the antibody is raised from an immunogen of the following structure:

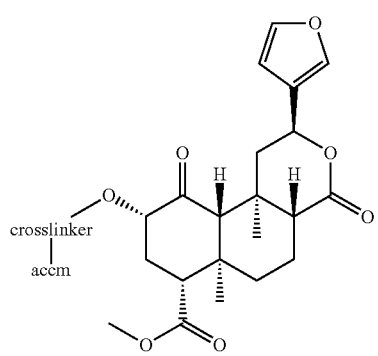

wherein accm is an antigenicity-conferring carrier material and the crosslinker joins the O-atom at C-9 of the tricyclic fused ring to the accm; and the conjugate comprises a reporter group that is linked to the O-atom at C-9 of the tricyclic fused ring of salvinorin B.

2. The method of claim 1, wherein the crosslinker is —$(X)_n$—Y—Z—, where n=0 or 1, and if present, X is selected from the group consisting of carbonyl, thiocarbonyl, oxycarbonyl and oxythiocarbonyl; Y is a $C_1$-$C_{10}$ substituted or unsubstituted straight chain or saturated alkylene moiety or arylene moiety and Z is selected from the group consisting of a carbonyl group or an amino group.

3. The method of claim 2, wherein Y is a $C_2$-$C_6$ substituted or unsubstituted straight chain or saturated alkylene moiety or an arylene moiety.

4. The method of claim 1, wherein the C-9 analogue is 9-methoxymethyl ethersalvinorin B or 9-ethoxymethylethersalvinorin B.

* * * * *

UNITED STATES PATENT AND TRADEMARK OFFICE
CERTIFICATE OF CORRECTION

PATENT NO. : 9,222,949 B2
APPLICATION NO. : 12/662651
DATED : December 29, 2015
INVENTOR(S) : Stephen Peter Fitzgerald et al.

It is certified that error appears in the above-identified patent and that said Letters Patent is hereby corrected as shown below:

In The Specification

Column 7, lines 12-13, "such as "EvidenceT'" or "Evidence InvestigatorT'"." should read:
--such as "Evidence™" or "Evidence Investigator™".--

Column 9, line 43, "Conjugation of Hapten A to HItP (Conjugate I)" should read:
--Conjugation of Hapten A to HRP (Conjugate I)--

Signed and Sealed this
Nineteenth Day of July, 2016

Michelle K. Lee
*Director of the United States Patent and Trademark Office*